(12) United States Patent
Hofler et al.

(10) Patent No.: US 9,498,571 B2
(45) Date of Patent: *Nov. 22, 2016

(54) NITRIC OXIDE DELIVERY DEVICES

(71) Applicant: The Regents of the University of Michigan, Ann Arbor, MI (US)

(72) Inventors: Lajos Hofler, Oxford (GB); Mark E. Meyerhoff, Ann Arbor, MI (US); Dipankar Koley, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 649 days.

This patent is subject to a terminal disclaimer.

(21) Appl. No.: 13/852,841

(22) Filed: Mar. 28, 2013

(65) Prior Publication Data

US 2013/0261537 A1    Oct. 3, 2013

Related U.S. Application Data

(60) Provisional application No. 61/617,886, filed on Mar. 30, 2012.

(51) Int. Cl.
*A61M 5/14* (2006.01)
*A61M 25/00* (2006.01)
(Continued)

(52) U.S. Cl.
CPC .......... *A61M 5/14* (2013.01); *A61K 33/00* (2013.01); *A61M 25/00* (2013.01);
(Continued)

(58) Field of Classification Search
CPC .......... A61M 2202/0275; A61M 2205/0272; A61M 2205/0233; A61M 2025/0057; A61M 25/0043; A61M 2005/066; A61M 2202/02; A61M 2202/0266; A61M 2205/3324; C10B 21/24

USPC .......... 604/23; 424/424, 425, 718; 423/405
See application file for complete search history.

(56) References Cited

U.S. PATENT DOCUMENTS 3,726,777 A * 4/1973 Macur ............... A61B 5/14539
  204/403.01
4,834,101 A    5/1989 Collison et al.
(Continued)

FOREIGN PATENT DOCUMENTS

WO    WO 95-07610    3/1995

OTHER PUBLICATIONS

Oh, Bong Kyun, et al., Catalytic Generation of Nitric Oxide from Nitrite at the Interface of Polymeric Films Doped with Lipphilic Cu(II)-complex: A potential Route to the Preparation of Thromboresistant Coatings, Biomaterials, Jan. 2004, vol. 25, No. 2 pp. 283-293.

(Continued)

*Primary Examiner* — Bhisma Mehta
*Assistant Examiner* — Jenna Zhang
(74) *Attorney, Agent, or Firm* — Dierker & Kavanaugh, P.C.

(57) ABSTRACT

A nitric oxide delivery device includes a housing that is permeable to nitric oxide. The surface of the housing is modified to detect surface charge or pH (e.g., due to cell adhesion). A working electrode (which is a copper-containing conductive material or a base material coated with a copper-containing conductive material) is positioned inside of the housing. A reference/counter electrode is also positioned inside of the housing, and is electrically isolated from the working electrode. A source of nitrite ions is to be contained within the housing such that it is in contact with the working electrode.

13 Claims, 8 Drawing Sheets

(51) Int. Cl.
*A61K 33/00* (2006.01)
*C01B 21/24* (2006.01)

(52) U.S. Cl.
CPC ......... *A61M 25/0043* (2013.01); *C01B 21/24* (2013.01); *A61M 2025/0057* (2013.01); *A61M 2202/0275* (2013.01); *A61M 2205/0233* (2013.01); *A61M 2205/0272* (2013.01)

(56) References Cited

U.S. PATENT DOCUMENTS

| | | | | |
|---|---|---|---|---|
| 5,396,882 | A | * | 3/1995 | Zapol .................... A61M 15/02 128/200.14 |
| 5,827,420 | A | * | 10/1998 | Shirazi .................. A61M 16/10 205/220 |
| 6,097,976 | A | * | 8/2000 | Yang ..................... A61L 29/085 600/373 |
| 7,407,570 | B2 | * | 8/2008 | Prince ............. G01N 33/48785 204/416 |
| 2003/0064028 | A1 | | 4/2003 | Fine et al. |
| 2004/0224868 | A1 | * | 11/2004 | Meyerhoff ............. A61K 33/34 510/320 |
| 2006/0008529 | A1 | * | 1/2006 | Meyerhoff .............. A61L 33/06 424/486 |
| 2007/0270674 | A1 | * | 11/2007 | Kane ................... A61B 5/14546 600/315 |
| 2008/0226686 | A1 | * | 9/2008 | Meyerhoff ............. A61K 33/34 424/422 |
| 2008/0262330 | A1 | * | 10/2008 | Reynolds ............... C12Q 1/003 600/347 |
| 2010/0051480 | A1 | * | 3/2010 | Schoenfisch ....... G01N 27/4045 205/781 |

OTHER PUBLICATIONS

Oh, Bong Kyun, et al., "Catalytic generation of nitric oxide from nitrite at the interface of polymeric films doped with lipophilic Cu(II)-complex: a potential route to the preparation of thromboresistant coatings", Biomaterials 25 (2004), pp. 283-293.

International Search Report and Written Opinion for PCT/US2013/034425 dated Jul. 18, 2013, 17 pages.

Hofler, Lajos, et al., "Electromodulated release of nitric oxide through polymer material from reservoir of inorganic nitrite salt", RSC Advances, Jul. 12, 2012, 3 pages.

* cited by examiner

NITRIC OXIDE DELIVERY DEVICES

CROSS-REFERENCE TO RELATED APPLICATIONS

This application claims the benefit of U.S. Provisional Application Ser. No. 61/617,886, filed Mar. 30, 2012, which is incorporated by reference herein in its entirety.

STATEMENT REGARDING FEDERALLY SPONSORED RESEARCH OR DEVELOPMENT

This invention was made with government support under Grant Nos. EB-000783 and EB-004527 awarded by the National Institutes of Health (NIH). The government has certain rights in the invention.

BACKGROUND

Nitric oxide (NO) has been shown to have several important physiological functions, including its unique vasodilating properties, cancer-fighting potency, anti-platelet activity, and anti-microbial/anti-viral activity. In some instances, NO can be used to control infection, prevent biofilm formation, and minimize inflammation and fibrosis. Although NO is a stable radical, it is highly reactive with hemoglobin and oxygen, thus making delivery of NO to the target site challenging. Stable hydrophilic, as well as hydrophobic NO donors may be employed to take advantage of the potency of NO for a wide range of biomedical applications. NO release polymeric materials and coatings based on diazeniumdiolate chemistry have been used to inhibit platelet adhesion. While these materials and coatings do exhibit NO release, the instability of diazeniumdiolates and other NO donors (e.g., S-nitrosothiols) render the commercialization of these materials and coatings challenging. For example, (Z)-1-[N-methyl-N-[6-(N-methylammoniohexyl)amino]]-diazen-1-ium-1,2-diolate (MAHMA/NO) dispersed in a silicone rubber matrix may, in some instances, prevent thrombus formation on the surface of intravascular sensors. MAHMA/NO may also greatly reduce platelet activity when employed within a polymer coating on the inner walls of extracorporeal circuits. However, MAHMA/NO and its corresponding diamine precursor tend to leach from the surface of the polymer matrix and back react with an oxidative intermediate of NO to form potentially toxic nitrosamines.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

The present disclosure relates generally to nitric oxide delivery devices. Examples of the nitric oxide delivery device disclosed herein enable one to perform a pulsed electrochemical method within gas permeable polymeric materials to generate and modulate the release of nitric oxide (NO) through the gas permeable polymeric material. The nitric oxide is electrochemically generated by the reduction of nitrite ions by Cu(I) ions, which are generated at the surface of a working electrode that is made of a copper containing conductive material, or a base material coated with a copper containing conductive material. In some instances, the pulsed electrochemical method is triggered in response to a detected change in potential or pH (e.g., at the surface of a catheter). It has also been found that during NO generation, the working electrode becomes passivated, for example, with an oxide or hydroxide layer, which can inhibit or deleteriously impact the ability to generate of NO. Examples of the method disclosed herein involve a two-step applied potential sequence, where one step generates Cu(I) ions and thus NO, and the other step cleans and refreshes the passivated working electrode surface. The cleaning and refreshing step prepares the working electrode surface for subsequent NO generation.

A copper containing conductive material is any material that contains copper and is able to release Cu(I) when an appropriate potential is applied. Examples of these materials include copper or copper alloys. The copper containing conductive material may be in the form of a wire, a mesh, an ink or paint that is applied to a surface (e.g., on an inner surface of the housing), copper nanoparticles that are incorporated/embedded into an electrically conducting polymer matrix or a conductive carbon paste, or any other desirable form. One example of the copper containing conductive material is a copper wire material.

Any of the examples of the nitric oxide delivery device disclosed herein may be a two electrode or a three electrode system. Some examples of the two electrode system are shown in FIGS. 1A, 2A, 2B, 3A and 3B, while an example of the three electrode system is shown in FIG. 1B. In the two electrode configurations, a working electrode and a reference or counter electrode (referred to herein as a reference/counter electrode) are used and current passes through the reference/counter electrode. In the three electrode configurations, a working electrode, a reference electrode and a counter electrode are used. In these systems, the applied voltage is measured versus the reference electrode, but the current passes through the counter electrode. A potentiostat may be used to operate the circuit when either the two or the three electrode system is used.

Figure 1A:
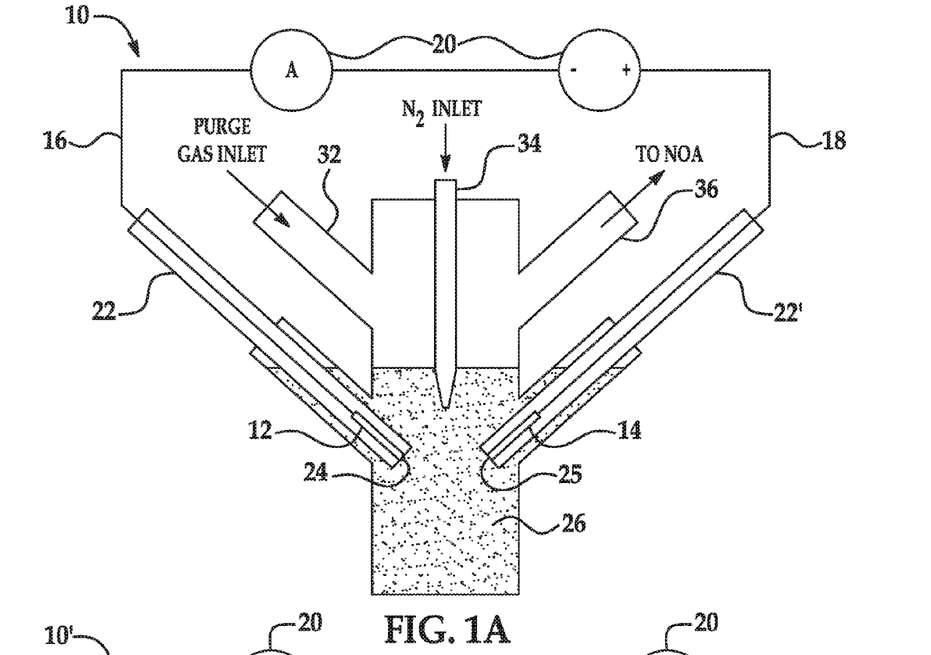
FIG. 1A is a schematic view of an example of a nitric oxide delivery device including a two-electrode configuration.
Figure 1B:
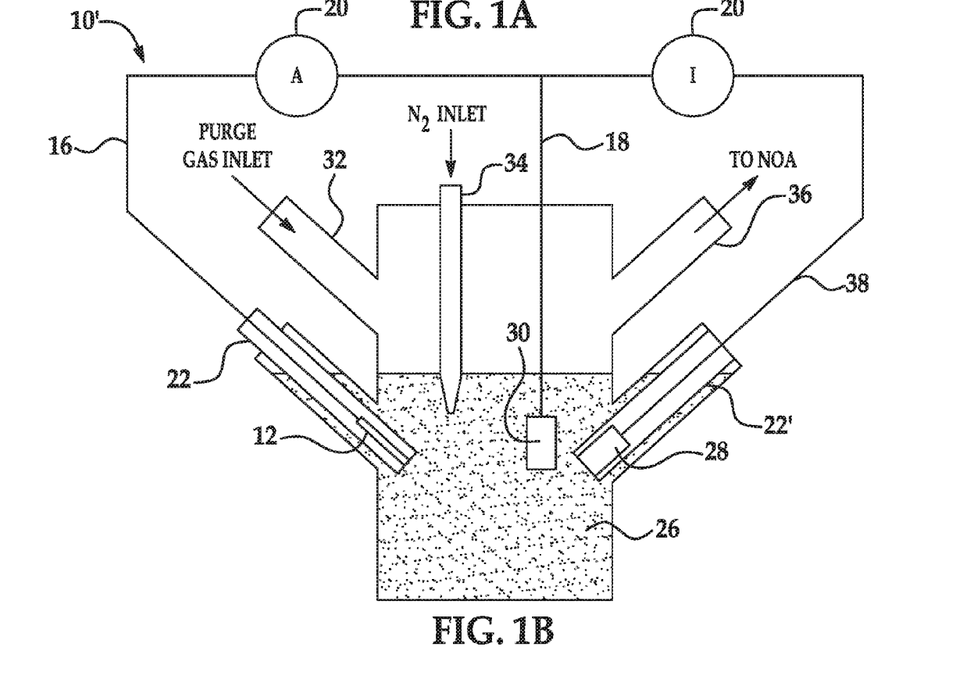
FIG. 1B is a schematic view of an example of the nitric oxide delivery device including a three-electrode configuration.

Referring now to FIGS. 1A and 1B, schemes of electrochemical generation of nitric oxide using the working electrode 12 in a two electrode system 10 and a three electrode system 10' are respectively depicted. In these example systems 10, 10', the generated nitric oxide is transferred to a nitric oxide analyzer NOA (e.g., a nitric oxide chemiluminescence analyzer) via an outlet 36 for quantitation of the amount of NO generated. The systems 10, 10' also include a purge gas inlet 32 and an $N_2$ gas inlet 34, which may be used to purge samples (e.g., the source of nitrite ions 26) during operation of the systems 10, 10'. While these systems 10, 10' may be used to generate NO using the methods disclosed herein, it is to be understood that the schemes of electrochemical generation illustrated in FIGS. 1A and 1B may be implemented into other devices, such as catheters (shown as reference numeral 100 in FIGS. 2A and 2B) and patches (shown as reference numeral 100' in FIG. 3A). These devices 100, 100' release the generated NO into the surrounding environment (as opposed to transferring the NO to the NO analyzer for quantitation) through the walls of the catheter tubing or through the planar patch material. As such, in reference to FIGS. 1A and 1B, the schemes of electrochemical generation will be described, and in reference to FIGS. 2A through 3B, various examples of the devices incorporating examples of these schemes will be described.

Referring now to FIG. 1A, the two electrode system 10 includes the working electrode 12 and the reference/counter electrode 14. The working electrode 12 may be an electrode made of the copper containing conductive material or another electrode (e.g., platinum, gold, carbon, mercury, etc.) coated with the copper containing conductive material. The reference/counter electrode 14 may be silver/silver chloride or some other reference electrode or pseudo reference electrode.

Conductive leads 16, 18 are respectively and electrically connected to the working electrode 12 and the reference/counter electrode 14. The conductive leads 16, 18 electrically connect the respective electrodes 12, 14 to the electronics 20 (e.g., a potentiostat) that are used to control the applied voltage, and in some instances, record potential shift changes and compare potential shift changes to a preset threshold value. Conductive leads 16, 18 may be made of any conductive material, examples of which include copper wires, platinum wires, stainless steel wires, aluminum wires, etc.

The working electrode 12 in FIG. 1A is shown in a glass tube 22, which is configured so that an end 24 of the working electrode 12 is exposed to the source of nitrite ions 26, but the source of nitrite ions 26 does not enter the tube 22. The reference/counter electrode 14 may also be contained within a glass tube 22'. The tube 22' is configured so that an end 25 of the reference/counter electrode 14 is exposed to the source of nitrite ions 26, but the source of nitrite ions 26 does not enter the tube 22'.

In an example, the source of nitrite ions 26 may be a water soluble, inorganic nitrite salt in an aqueous solution or within a hydrogel (e.g., hydroxymethylcellulose, poly(vinyl alcohol) (PVA), gelatin, etc.). Some examples of water soluble, inorganic nitrite salts include alkali metal and alkaline earth metal nitrite salts. Specific examples include nitrite salts of Li, Na, K, Rb, Ca, and Mg. Most other metal salts are also soluble in water, for example, Al salts and Fe salts. One specific example of the source of nitrite 26 is $NaNO_2$.

In another example, the source of nitrite 26 may be a lipophilic quaternary ammonium nitrite species soluble in an organic polymeric phase. This particular source of nitrite 26 may not be suitable for the examples of the catheter disclosed herein that have a modified wall/exterior surface. For the other examples that may include the lipophilic quaternary ammonium nitrite species, the lipophilic quaternary ammonium nitrite salt may be chosen from tetradodecylammonium nitrite, tridodecylmethylammonium nitrite, tetradecylammonium nitrite, and tetraoctylammonium nitrite. The organic polymeric phase may be chosen from polyurethane, poly(vinyl chloride), polymethacrylate, and polydimethylsiloxane (PDMS). The organic polymeric phase may be doped with a relatively high concentration of the lipophilic quaternary ammonium nitrite salt. The high concentration of the lipophilic quaternary ammonium nitrite salt will depend, at least in part, on the polymer matrix used. In an example, the high concentration ranges from about 1 mM to about 300 mM. In one example when the lipophilic quaternary ammonium nitrite species is used as the source of nitrite ions 26, the working electrode 12 (i.e., the source of Cu(I)) may be nanoparticles of the copper containing conductive material embedded in the organic polymer phase.

The source of nitrite ions 26 may also include a buffer and/or another additive that aids in driving the reduction reaction of Cu(I) with nitrite. An example of a suitable buffer is phosphate buffered saline (PBS). An example of the other suitable additive is ethylenediaminetetraacetic acid (EDTA). EDTA helps drive the reduction reaction of Cu(I) with nitrite $(Cu(I)+NO_2^-+2H^+\rightarrow Cu(II)+NO+H_2O)$ to the product side by chelating with Cu(II) stronger than with Cu(I). As an example, the source of nitrite ions 26 includes 1 M $NaNO_2$, 25 mM EDTA and 0.138 M NaCl in 1 M phosphate buffer (pH 7.2).

Electrochemical generation of nitric oxide using the two electrode system 10 of FIG. 1A involves application of voltage pulses to the working electrode 12, where current passes through the reference/counter electrode 14. A cathodic voltage pulse is applied to the working electrode 12 to clean the surface (including the end 24) of the working electrode 12. The cathodic pulse may be applied for a period of time that is suitable for refreshing the working electrode 12 surface. In an example, the time for which the cathodic pulse is applied ranges from about 1 second to about 10 minutes. Then, an anodic voltage pulse is applied to the working electrode 12. The anodic voltage pulse produces a low concentration of Cu(I) ions at the electrode 12 surface. The Cu(I) ions produced at the end 24 react directly with nitrite in the source of nitrite ions 26 to generate nitric oxide gas. The anodic voltage pulse is applied to the working electrode 12 for a limited time interval ranging from about 1 second to about 10 minutes, at least in part because Cu$_2$O/CuOH forms on the electrode 12 when the anodic voltage pulse is applied. The oxide formed on the surface of the working electrode 12 interferes with the generation of nitric oxide gas. When it is desired to generate NO again, the cathodic pulse is applied to clean the electrode 12, and then the anodic pulse is applied to generate NO. To observe consistent reduction of nitrite to NO, the two-step potential sequence (i.e., cathodic pulse followed by anodic pulse) is continuously and repeatedly applied to the working electrode 12.

It is to be understood that the time frames provided for application of the cathodic voltage pulse and the anodic voltage pulse are examples and may be varied depending upon the amount of NO to be generated and/or the time needed to refresh the working electrode 12 surface. Generally, if less Cu(I) is generated during the anodic step, than the cathodic step will be shorter because less time is needed to refresh the working electrode surface. As an example, it is believed that a cycle that includes a 5 second cathodic pulse and a 5 second anodic pulse may be used. In this example, the NO production may be relatively low due, at least in part, to rapid depletion of nitrite near the working electrode 12. Nitrite arrives at the electrode 12 surface by diffusion, and the rate of NO production may be faster than the rate of nitrite diffusion. However, such low levels of NO may be desirable in some instances.

Referring now to FIG. 1B, the three electrode system 10' includes the working electrode 12, the reference electrode 28, and the counter electrode 30. In an example, the reference electrode 28 is silver/silver chloride and the counter electrode 30 is platinum. In the three electrode system 10', the reference electrode 28 may also be an ion-selective pseudo-reference electrode (e.g., a sodium-selective electrode or a potassium-selective electrode). Conductive leads 16, 18 are respectively and electrically connected to the working electrode 12 and the counter electrode 30. A conductive lead 38 electrically connects the reference electrode 28 to the working and counter electrodes 12, 30. The conductive leads 16, 18, 38 electrically connect the respective electrodes 12, 30, 28 to the electronics 20 (e.g., a potentiostat) that are used to control the applied voltages, and in some instances, record potential shift changes and compare potential shift changes to a preset threshold value. The conductive leads 16, 18, 38 may be made of any of the conductive materials previously described.

In FIG. 1B, the working electrode 12 is set up in a similar manner to that described in reference to FIG. 1A. Also in FIG. 1B, the counter electrode 30 is set up in a similar manner to that described for the reference/counter electrode 14 in reference to FIG. 1A. The counter electrode 30 used in the three electrode system 10' may be inserted into the source of nitrite ions 26. Electrochemical generation of nitric oxide using the three electrode system 10' of FIG. 1B involves application of voltage pulses to the working electrode 12, where current passes through the counter electrode 30. The voltage applied to the working electrode 12 and through the counter electrode 30 is measured against the reference electrode 28. This system 10' may be used to apply the previously described two-step potential sequence (i.e., cathodic pulse followed by anodic pulse) to the working electrode 12 to generate NO.

Figures 2A, 2B, 2C:
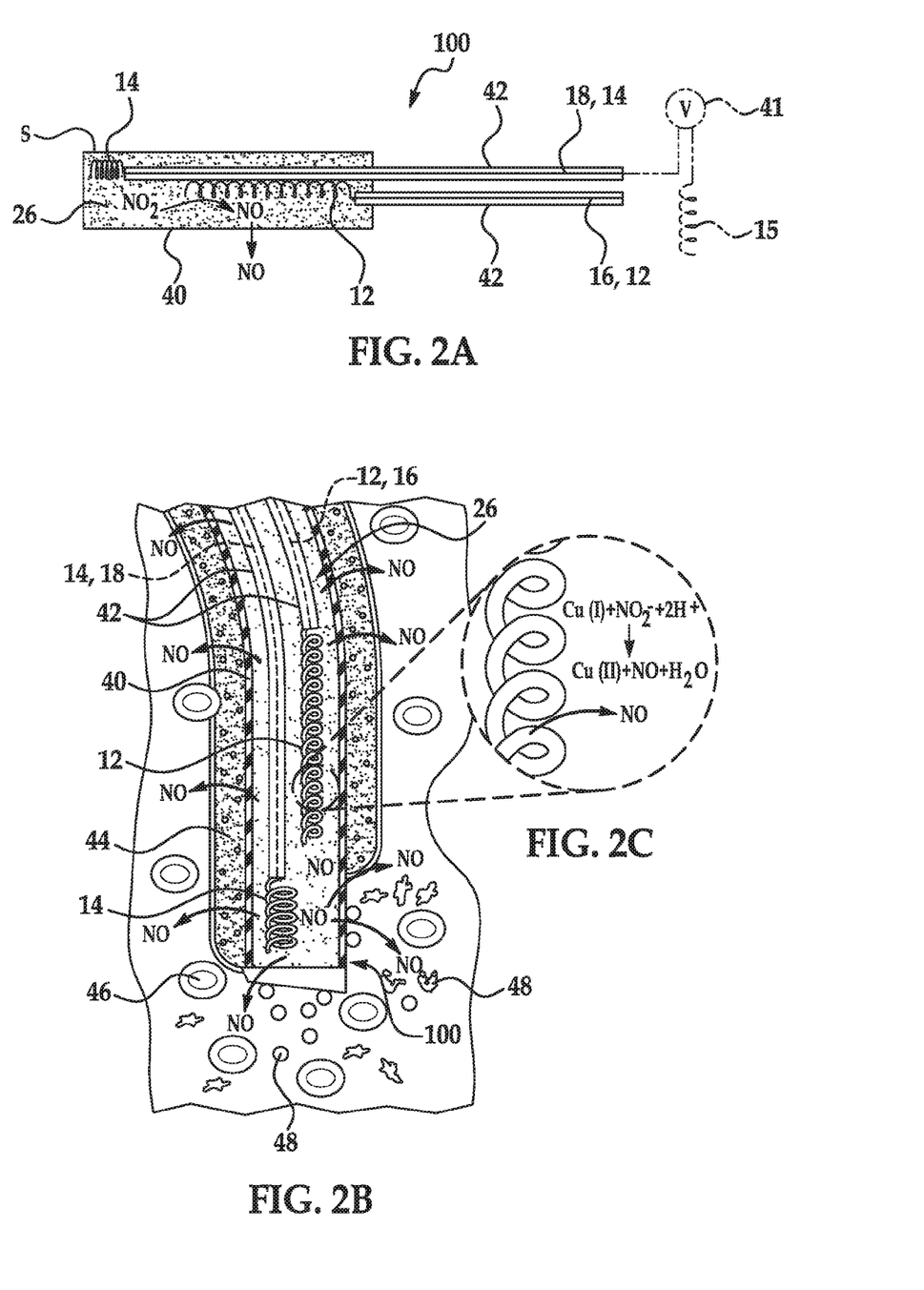
FIG. 2A is a schematic view of another example of the nitric oxide delivery device in the form of a catheter.
FIG. 2B is a schematic, partially cross-sectional view of an example of the catheter positioned in a blood vessel.
FIG. 2C is an enlarged, schematic view of the chemical reaction taking place at the working electrode in the catheter of FIG. 2B.
Figure 3A:
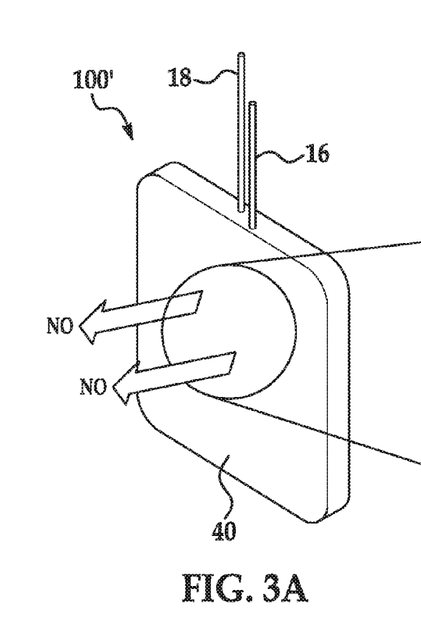
FIG. 3A is a schematic view of another example of the nitric oxide delivery device in the form of a planar patch.
Figure 3B:
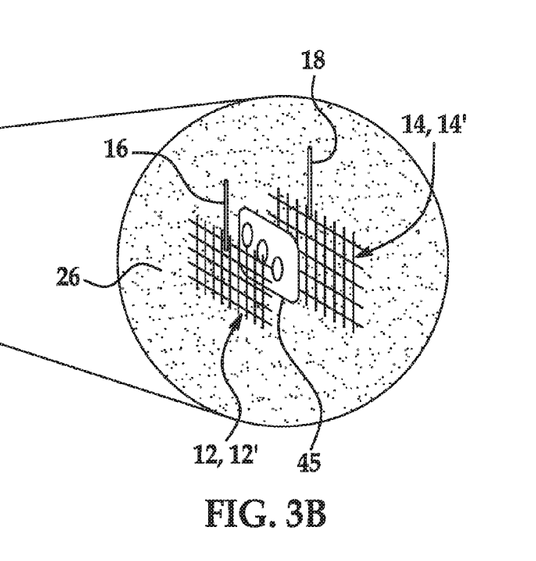
FIG. 3B is an enlarged view of the inside of the planar patch of FIG. 3A.

Some of the components of the systems 10, 10' of FIGS. 1A and 1B may be incorporated into medical devices, such as catheters 100 (shown in FIGS. 2A and 2B) or planar patches 100' (shown in FIGS. 3A and 3B). These devices 100, 100' may be operated to selectively generate NO as described above. In some examples, the catheter 100 may be configured to detect the presence of bacteria (e.g., biofilm) on its surface, and in response, generate NO to disperse the attached bacteria and keep the surface free of bacteria. In the devices 100, 100', the electronics that apply the desired potentials, and in some instances record and compare potential shifts and values, may be minimized to be secured to the housing 40 of the respective devices 100, 100' and may be operated via a battery or another source of energy (e.g., solar generator, an energy harvesting device, etc.). Furthermore, while the following description relates to examples of the two electrode system, it is to be understood that the three electrode system may also be implemented into the medical devices.

Referring now to FIG. 2A, the catheter 100 illustrated is a two electrode system (similar to system 10) that includes a housing 40 that is permeable to nitric oxide. The housing 40 keeps the source of nitrite ions 26 and the electrodes 12, 14 separated from the external environment. The housing material is selected so as to prevent the source of nitrite ions 26 from leaking out of the housing 40 while allowing NO gas to permeate through the housing 40 to the external environment. Examples of suitable materials for the housing 40 include silicone rubber, biomedical grade polyurethane, polytetrafluoroethylene (PTFE), polytetrafluoroethylene derivatives (e.g., ethylene tetrafluoroethylene (ETFE), fluorinated ethylene-propylene (FEP), perfluoroalkoxy (PFA), etc.), polymethacrylate, and poly(vinyl chloride). The housing 40 used in the catheter may have a cylindrical geometry.

Both the working electrode 12 and the reference/counter electrode 14 are positioned within the housing 40. The electrodes 12, 14 are positioned such that they are electrically isolated from one another. The exposed electrodes 12, 14 may be physically separated from one another. As shown in FIG. 2A, in an example, a portion of the reference/counter electrode 14 that is adjacent to the working electrode 12 within the housing 40 may be coated with an insulating layer 42 in order to ensure electrical isolation of the two electrodes 12, 14. This insulating layer 42 is described further hereinbelow.

Conductive leads 16, 18 are electrically connected to the respective electrodes 12, 14. The leads 16, 18 may be part of the respective electrodes 12, 14, or may be separate wires that are electrically connected to the respective electrodes 12, 14. The leads 16, 18 extend from the electrodes 12, 14 (which are inside the housing 40) to electronics (not shown) which are outside of the housing 40. FIG. 2A illustrates an example in which the leads 16, 18 are part of the respective electrodes 12, 14. In this example, the working electrode 12 includes the coiled portion within the housing 40, and the lead portion 16 extending outside of the housing 40. Also in this example, the reference/counter electrode 14 includes the coiled portion within the housing 40, and the lead portion 18 that is partially inside of the housing and partially outside of the housing 40. In examples in which the leads 16, 18 are separate wires that are connected to the electrodes 12, 14, it is to be understood that the leads 16, 18 may be the same material as, or different materials than the electrodes 12, 14.

The housing 40 may be sealed at areas where the leads 16, 18 pass therethrough. In an example, the housing 40 is sealed using a silicone rubber seal/sealant.

The housing 40 also contains the source of nitrite ions 26. Any of the sources previously described may be used in this example device 100. The source of nitrite ions 26 is contained within the housing 40 such that the working electrode 12 and the reference/counter electrode 14 are in contact with the source of nitrite ions 26.

While not shown in FIG. 2A, it is to be understood that the working electrode 12 may be formed of an ink or paint that includes the copper containing conductive material, and the reference/counter electrode 14 may be formed of an ink or paint that includes silver or another suitable conductive material. In this example, the electrodes 12, 14 may be screen printed or otherwise formed on the inner walls of the housing 40.

As briefly mentioned above, areas or portions of one or more of the electrodes 12, 14 and/or the leads 16, 18 may be coated with an insulating layer 42. As illustrated in FIG. 2A, a portion of the reference/counter electrode 14 that is adjacent to the working electrode 12 within the housing 40 may be coated with the insulating layer 42. In this example, at least a portion of the reference/counter electrode 14 within the housing 40 (e.g., the coiled portion shown in FIG. 2A) remains exposed. Also as illustrated in FIG. 2A, the leads 16, 18 may be coated with the insulating layer 42. In these examples, ends of the leads 16, 18 may remain exposed to electrically connect to suitable electronics. Any insulating material may be used for the insulating layer 42, examples of which include polytetrafluoroethylene (PTFE), polyethylene, silicone, etc. In other examples, the electrodes 12, 14 and/or the leads 16, 18 may remain uncoated.

Electrochemical generation of nitric oxide using the catheter 100 of FIG. 2A involves application of a cathodic voltage pulse to the working electrode 12 to clean the surface of the working electrode 12, and then application of an anodic voltage pulse to the working electrode 12 to produce a concentration of Cu(I) ions at the electrode 12 surface. The Cu(I) ions produced at the surface react directly with nitrite in the source of nitrite ions 26 to generate nitric oxide gas, which permeates through the housing 40 to the external environment.

As previously mentioned, the potential applied to the working electrode 12 may be controlled to turn NO release on or off. An advantage of this control is that nitrite salts may be dissolved in high concentrations and incorporated into reservoirs in the lumen of the catheter 100. As an example, one lumen of a dual lumen biomedical catheter may be used as a nitrite salt reservoir, and the second lumen may be used to sample blood, infuse therapeutic agents, etc. It is believed that a 150 μm thick layer of a 1 M nitrite solution can produce a $1\times10^{-10}$ mol·min$^{-1}$·cm$^{-2}$ NO flux continuously for at least 100 days in a cylindrical arrangement (e.g., a catheter) or planar arrangement (e.g., the patch described below).

It is to be understood that while illustrated as a single lumen catheter configuration in FIG. 2A, in other examples (e.g., when to be used in clinical practice), the electrochemical generating concept disclosed herein may be implemented using a multi-lumen catheter. In the multi-lumen example, one lumen may be dedicated for NO generation, while blood can be removed through an open lumen of the catheter, or therapeutic solutions can be infused into a patient through the open lumen(s).

The wall, and thus the exterior surface S, of the housing 40 may be modified to detect any charged species (e.g., negatively charged or positively charged bacteria) that is sitting on the exterior surface S. Bacteria, and in particular biofilm, that forms on the exterior surface S of the catheter 100 may contribute to catheter related infections. The catheter 100 having the modified surface can detect the bacteria, and in response, can initiate NO generation from within the housing 40. The catheter 100 can release NO that is generated the electrochemical pulse method disclosed herein. The released NO acts as an effective antimicrobial and biofilm dispersal agent. The released NO may also exhibit potent antithrombotic activity.

The wall and exterior surface S of the housing 40 may be modified with any additive(s) that will render the surface S with the ability to detect charge on the surface S. In an example, the additive(s) are impregnated into the exterior surface S. It is to be understood that any of the housing materials mentioned herein may be modified with a cation/anionic salt and a plasticizer. Examples of the cation/anionic salt include tetradodecylammonium tetrakis (4-chlorophenyl) borate, tridodecylmethylammonium tetrakis (bis-trifluormethylphenyl borate), etc. Examples of the plasticizer include dibutyl sebacate, dioctyl sebacate, nitrophenyloctyl ether, etc. In an example, silicone tubing is impregnated with tetradodecylammonium tetrakis (4-chlorophenyl) borate and dioctyl sebacate in an m-xylene solution.

In an example, the modified exterior surface S is capable of detecting charged species that are in contact with the surface S. The electronics operatively connected to the catheter 100 are able to record negative and positive potential shifts, which depend upon the number of bacteria on the surface S of the catheter 100. The potential shifts are measured from an initial operating potential of the catheter 100 (i.e., a background potential). In general, more bacteria present on the surface S results in a greater negative or positive potential shift from the background potential. Storage/memory associated with the electronics may be programmed with a threshold value of potential shift. The threshold value of potential shift may be based upon an undesired number of bacteria present on the surface S. For example, it may be determined that a 100 mV shift in potential is an indication of a critical mass of bacteria on the surface S, and this value may be stored as the threshold value to which recorded values are compared. When the amount of bacteria present on the surface S reaches the undesired number, the recorded potential shift will exceed the threshold value. In an example, the potential shifts are recorded by a high impedance voltmeter 41 (shown in FIG. 2A).

The electronics (which may include a controller running computer readable code) are also configured to recognize that the threshold value of potential shift has been reached or exceeded, and in response, will automatically trigger electrochemical NO production. In other words, upon recognizing that the recorded potential shift meets or exceeds the threshold value, the electronics will initiate the electrochemical pulse method disclosed herein. In an example, the electronics are configured to first apply a cathodic voltage pulse to the working electrode 12 to clean the surface of the electrode 12, and then apply an anodic voltage pulse to the working electrode 12 to produce a low concentration of Cu(I) ions at the working electrode 12 surface. The Cu(I) ions produced at the surface react directly with nitrite in the source of nitrite ions 26 to generate nitric oxide gas, which permeates through the housing 40 to the external environment. The released NO disperses the bacteria on the surface S. As a result of bacteria dispersal, the surface potential shifts back to the background value at which the catheter 100 was operating initially. Upon recognizing that that background potential is again reached, the electronics are configured to turn off NO generation (i.e., stop the electrochemical pulse method). The catheter 100 then operates at the background potential until the accumulation of bacteria on the surface S is enough to cause another potential shift.

FIG. 2B schematically illustrates an example of the catheter 100 positioned within a blood vessel 44 (also showing red blood cells 46). In this example, bacteria 48 on the surface S has been detected and a potential shift resulting from the bacteria 48 has been recognized as exceeding the pre-programmed threshold value. As such, electrochemical pulses have been initiated using electrodes 12, 14, and NO is generated. The reaction (i.e., $(Cu(I)+NO_2^-+2H^+ \rightarrow Cu(II)+NO+H_2O)$) taking place at the working electrode 12 is shown in FIG. 2C. The generated NO permeates through the housing 40 into the surrounding environment, where it contributes to the prevention of smooth muscle cell proliferation, the prevention of platelet activation/thrombosis, and kills bacteria 48.

In still another example, the housing 40 may be modified to detect localized pH changes at the exterior surface S. The housing wall and exterior surface S may be doped with a chemical (e.g., a pH sensitive material) that allows electrochemical detection of the pH changes. In an example, the housing 40 can be doped with any proton ionophore, such as tridodecylamine (TDDA), along with from about 10 mol % to about 50 mol % (relative to the ionophore) of any tetraphenylborate species (lipophilic anion site).

As shown in FIG. 2A, the pH sensitive catheter may be operated in combination with a reference electrode 15 external to the housing 40. The external reference electrode 15 facilitates monitoring of the potential across the pH sensitive housing 40, where the potential is a function of the pH of the external environment (including bacteria or other cells adhering to the external surface S) being monitored. As such, the potential between the reference/counter electrode 14 and the external reference electrode 15 tracks the pH of the external environment. In an example, a potential change due to any difference in proton activity at the exterior surface S of the housing 40 (measured using the external reference electrode 15 in contact with a solution outside of the housing 40) versus proton activity at the inner surface (i.e., pH buffer in the nitrite solution 26, measured using reference/counter electrode 14) may be detected using a high impedance voltmeter 41. This potential change indicates the presence of bacteria or other cells adhering to the exterior surface S of the catheter housing 40. A given pH change as determined from the measured potential will then trigger the electrochemical NO generation process, as described above when using surface charge to detect the presence of cells.

Referring now to FIGS. 3A and 3B, the planar patch 100' and an exploded view of its interior are respectively depicted. The planar patch 100' illustrated is a two electrode system (similar to system 10) that includes the housing 40 that is permeable to nitric oxide. The housing 40 of the planar patch 100' functions in the same manner as the housing 40 used for the catheter 100. In this example however, the housing 40 has the shape of a relatively flat cube, relatively flat rectangular box, or other relatively flat three-dimensional shape. The housing 40 does have a length, width, and a depth; however the depth may be relatively small so that the planar patch 100' is flexible and able to conform to the shape of a desired subject (e.g., a limb, appendage, etc. that the planar patch is affixed, adhered, or otherwise secured to). The planar patch 100' may also be constructed so that only the surface that is to be adjacent to the desired subject is made of the permeable material, while the remainder of the surfaces is impermeable to NO. In this example then, NO is releasable from the desired surface alone.

In this example, the working electrode 12 is a mesh 12', which may be a network of wires or screen printed lines. Similarly, the reference/counter electrode 14 is a metal-containing mesh 14', which may be a network of metal (Pt) or other conductive material (Ag/AgCl) wires or screen printed lines. In the planar patch 100', the working electrode 12 may also be formed of nanoparticles of the copper containing conductive material dissolved in a suitable polymer matrix.

The meshes 12', 14' (or the mesh 14' and the polymer matrix containing copper containing nanoparticles) are electrically isolated from one another by a separator 45. Examples of suitable separators 45 include polymeric materials, such as polyethylene, polypropylene, polytetrafluoroethylene, poly(vinyl chloride), or other like materials. While the separator 45 is electrically insulating, it is also capable of conducting ions (i.e., is ionically conducting).

Conductive leads 16, 18 are electrically connected to the respective electrode meshes 12', 14'. In this example, the leads are separate wires that are electrically connected to the respective meshes 12', 14'. The leads 16, 18 extend from the meshes 12', 14' (which are inside the housing 40) to electronics (not shown) which are outside of the housing 40.

The housing 40 also contains the source of nitrite ions 26. Any of the sources previously described may be used in this example device 100'. The source of nitrite ions 26 is contained within the housing 40 such that at least the working electrode mesh 12' is in contact with the source of nitrite ions 26.

Electrochemical generation of nitric oxide using the planar patch 100' of FIG. 3 involves application of a cathodic voltage pulse to the working electrode mesh 12' to clean the surface of the mesh 12', and then application of an anodic voltage pulse to the working electrode mesh 12' to produce a low concentration of Cu(I) ions at the mesh surface. The Cu(I) ions produced at the surface react directly with nitrite in the source of nitrite ions 26 to generate nitric oxide gas, which permeates through the housing 40 to the external environment. To observe consistent reduction of nitrite to NO, the two-step potential sequence (i.e., cathodic pulse followed by anodic pulse) is continuously and repeatedly applied to the working electrode mesh 12'.

The NO generation methods described herein may be controlled to selectively generate NO at a desired time. For example, control of the potential applied to the working electrode 12 can turn on the generation of NO or can turn off the generation of NO. For efficient bactericidal activity, it may be desirable to turn NO generation on and off at least once a day, where the on cycle ranges from about 1 hour to about 2 hours. In some instances, it may also be desirable to turn NO generation on and off multiple times within a day. In other examples, the device may be configured to sense the presence and/or absence of bacteria and, in response, turn on and/or off NO generation, respectively. The flux of NO that is generated may also be modulated by altering an amount of a surface area of the working electrode 12 or mesh 12' that is exposed to the source of nitrite ions 26 (e.g., changing the length of the electrode 12 or mesh 12'), by altering a concentration of nitrite in the source of nitrite ions 26, by altering a magnitude of the cathodic voltage and/or the anodic voltage, by altering the pH, and/or by altering the concentration of additive(s) that are included.

To further illustrate the present disclosure, examples are given herein. It is to be understood that these examples are provided for illustrative purposes and are not to be construed as limiting the scope of the present disclosure.

EXAMPLES

Example 1

A silicone rubber tubing (2 cm length, 0.51 mm inner diameter, and 0.94 mm outer diameter) was sealed at one end with silicone rubber sealant. A 2 cm long polytetrafluoroethylene (PTFE)-coated silver/silver chloride wire was used as the reference electrode, and a 2 cm long PTFE-coated copper wire was used as the working electrode. The bare copper wire had an outer diameter of 0.127 mm, and coated copper wire had an outer diameter of 0.152 mm. The PTFE was removed from the ends of the silver/silver chloride wire and the copper wire in 20 mm and 10 mm lengths, respectively. The exposed ends of the respective wires were coiled separately. The coiled ends were inserted into the silicone rubber tubing so that the silver/silver chloride wire and the copper wire were not in direct metallic connection.

A source of nitrite was loaded into the tubing. The source of nitrite included 1 M $NaNO_2$, 0.138 M NaCl, 0.02 M EDTA in 1 M phosphate buffered saline (PBS). The pH was adjusted to 6.8 with NaOH or using appropriate ratios of phosphate salts.

The silicone rubber tubing was then sealed to form a catheter. PTFE-coated silver/silver chloride wire and PTFE-coated copper wire extended out of the silicone rubber tubing as respective leads to the reference and working electrodes.

Figure 4A:
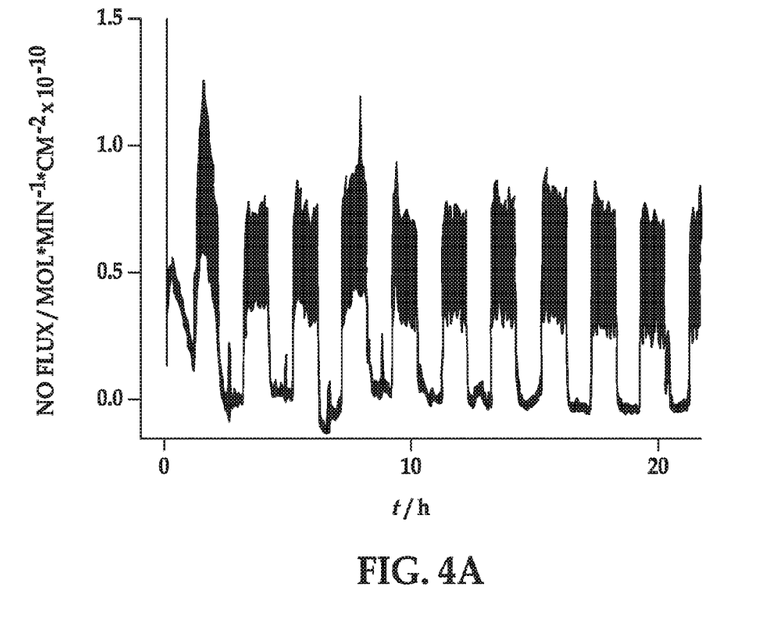
FIG. 4A is a graph illustrating the nitric oxide flux from an example of the nitric oxide delivery device over a 24 hour period.

A cathodic voltage (−0.7 V vs. NHE) was applied to the working electrode for about 3 minutes, and then an anodic voltage (+0.2 V vs. NHE) was applied to the working electrode for about 3 minutes. The pulse sequence was initiated for 1 hour every 2 hours over a 24 hour period. The NO flux from the surface of the silicone rubber tubing is shown in FIG. 4A. One 2 hour segment of FIG. 4A is shown expanded in FIG. 4B. The left hand side of the graph illustrates when the voltage cycle is turned off, and the right hand side of the graph illustrates when the voltage cycle is turned on.

Figure 4B:
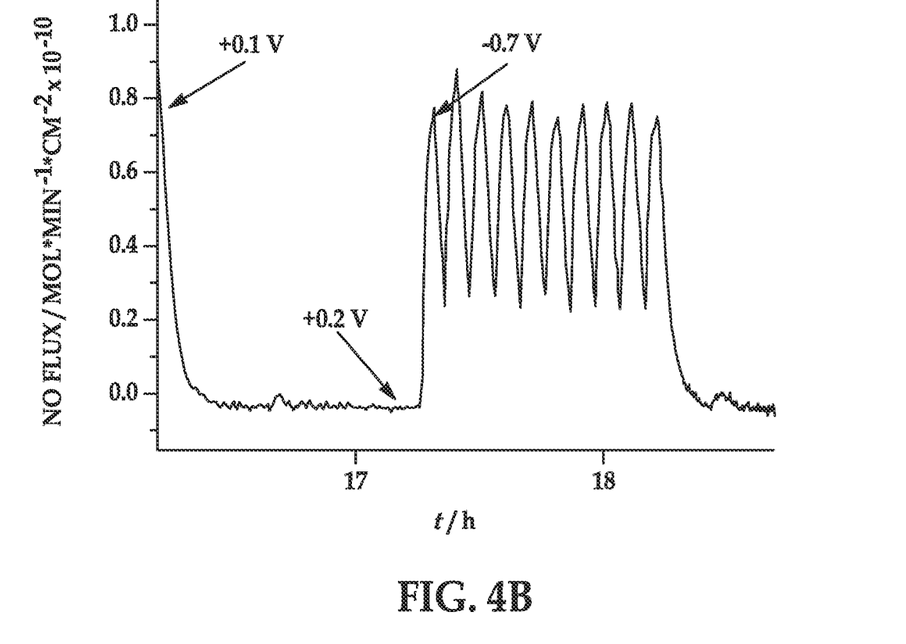
FIG. 4B is an expanded portion of the graph of FIG. 4A.

As illustrated in FIG. 4B, a catheter with a 2 cm long thin copper electrode was able to generate an average NO flux of $0.6 \times 10^{-10}$ mol·cm$^{-2}$·min$^{-1}$ when the previously described voltage cycle was implemented. In the absence of any voltage, nitric oxide was not generated and thus the NO flux was zero. It is noted that the average flux reported in this Example is based upon the surface area of the entire silicon rubber tubing, not the copper electrode alone. The results shown in FIG. 4A illustrate that the potential applied to the copper coated electrode can be controlled to turn on or off the release of NO through the walls of the silicone rubber tubing. The silicone rubber tubing provided a barrier against the leaching of nitrite from the catheter, but also allowed for the electrochemically generated NO gas to readily diffuse out of the catheter.

Example 2

A bacterial biofilm prevention study was performed using the NO generating catheters of Example 1. Two strains of bacteria were used, namely *E. coli* and *A. baumannii*.

The experiment was performed over a 1 week period with continuous flow of media using a Center for Disease Control (CDC) bioreactor. 4 NO generating catheters were immersed in the media containing either *E. coli* or *A. baumannii*. Two of the catheters were connected to an amperometric work station and a continuous potential program was applied to the respective working electrodes. The potential program included 3 minutes at −0.97 V vs. Ag/AgCl (−0.7 V vs. normal hydrogen electrode) for reduction, and −0.07 V vs. Ag/AgCl (+0.2 V vs. normal hydrogen electrode) for liberation of NO. The other two catheters were used as controls. These control catheters contained the same nitrite salt solution and wires, but were not linked to potentiostats.

Figure 5A:
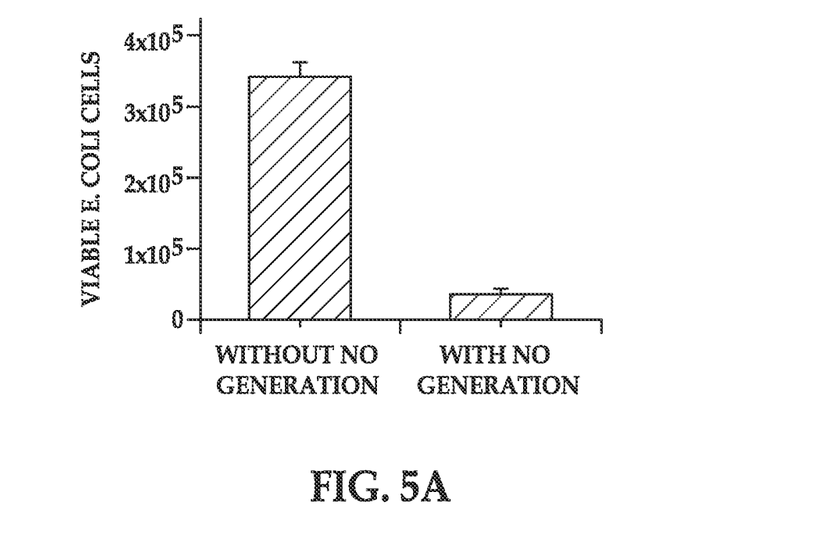
FIGS. 5A and 5B are graphs illustrating the effect of electrochemical generation of nitric oxide from a catheter surface on biofilm formation for *E Coli* (FIG. 5A) and *A. baumannii* (FIG. 5B)
Figure 5B:
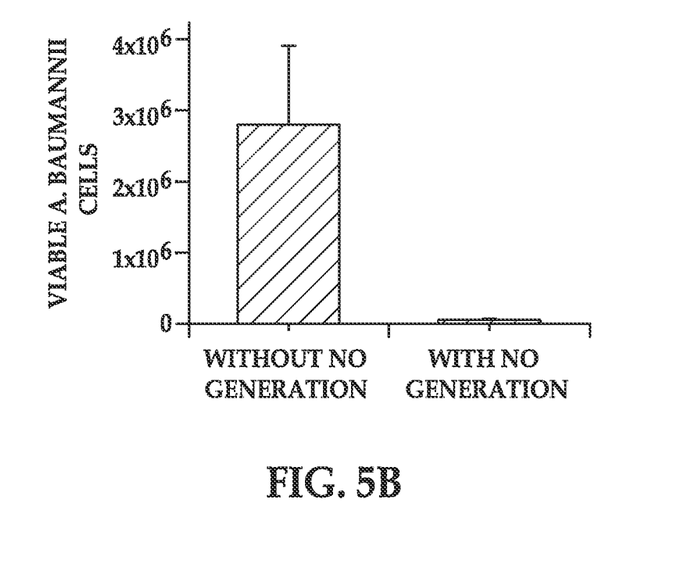

At the end of the one week period, the catheters were stained with fluorescent dyes (SYTO-9 and propidium iodide) for 20 minutes in the dark. The catheters were put on a glass slide before being observed with a fluorescence microscope equipped with Fluorescent Illumination System (X-cite 120, EXFO) and appropriate filter sets. FIGS. 5A and 5B illustrate the bacterium counting results after 7 days. These results are based upon the staining and fluorescence imaging discussed above. The bacterium counting results show that the NO generating catheters that released NO had 90% less viable *E. coli* on their surfaces, and had 98% less viable *A. baumannii* on their surfaces, when compared to the control catheters (which did not release NO).

Example 3

A three electrode system similar to that shown in FIG. 1B was used in this example. A 1 mm long copper electrode was used as the working electrode, a 0.5 mm long platinum wire was used as the counter electrode, and a silver/silver chloride electrode was used as the reference electrode.

Figure 6:
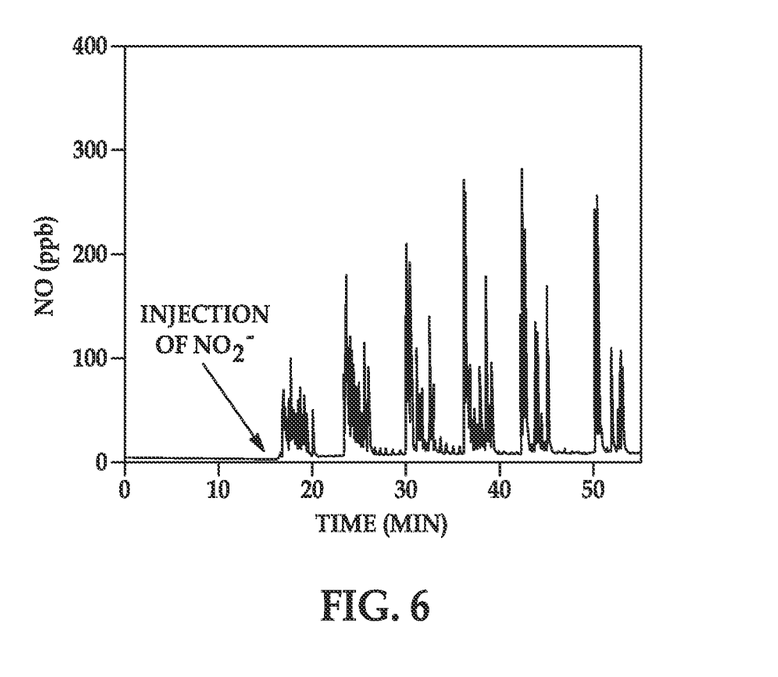
FIG. 6 is a graph illustrating the electrochemical generation of nitric oxide from a nitrite solution using an example of the nitric oxide delivery device disclosed herein.

The copper electrode was pulsed at −0.92 V (vs. Ag/AgCl) for about 3 minutes in the absence of $NO_2^-$ (i.e., in a 9 mL solution containing 50 mM EDTA and 10 mM NaCl). The potential at the copper electrode was then switched to +0.2 V (vs. Ag/AgCl), and 1 mL of 1 M $NaNO_2$ solution was injected into the 9 mL solution of EDTA and NaCl. The copper electrode was subsequently pulsed between +0.2 V and open circuit potential to turn NO generation on and off. The results are shown in FIG. 6. As illustrated, after the source of nitrite was injected, NO was generated during the +0.2 V portion of the cycle.

Example 4

A silicone rubber tubing (2 cm length, 0.51 mm inner diameter, and 0.94 mm outer diameter) was sealed at one end with silicone rubber sealant. A 2 cm long polytetrafluoroethylene (PTFE)-coated silver/silver chloride wire was used as the reference electrode, and a 2 cm long PTFE-coated copper wire was used as the working electrode. The bare copper wire had an outer diameter of 0.127 mm, and coated copper wire had an outer diameter of 0.152 mm. The PTFE was removed from the ends of the silver/silver chloride wire and the copper wire in 20 mm and 10 mm lengths, respectively. The exposed ends of the respective wires were coiled separately. The coiled ends were inserted into the silicone rubber tubing so that the silver/silver chloride wire and the copper wire were not in direct metallic connection.

A source of nitrite was loaded into the tubing. The source of nitrite included 1 M $NaNO_2$, 0.138 M NaCl, 25 mM EDTA in 1 M phosphate buffered saline (PBS). The pH was adjusted to 7.2 with NaOH or using appropriate ratios of phosphate salts.

The silicone rubber tubing was then sealed to form a catheter. PTFE-coated silver/silver chloride wire and PTFE-coated copper wire extended out of the silicone rubber tubing as respective leads to the reference and working electrodes.

Figure 7:
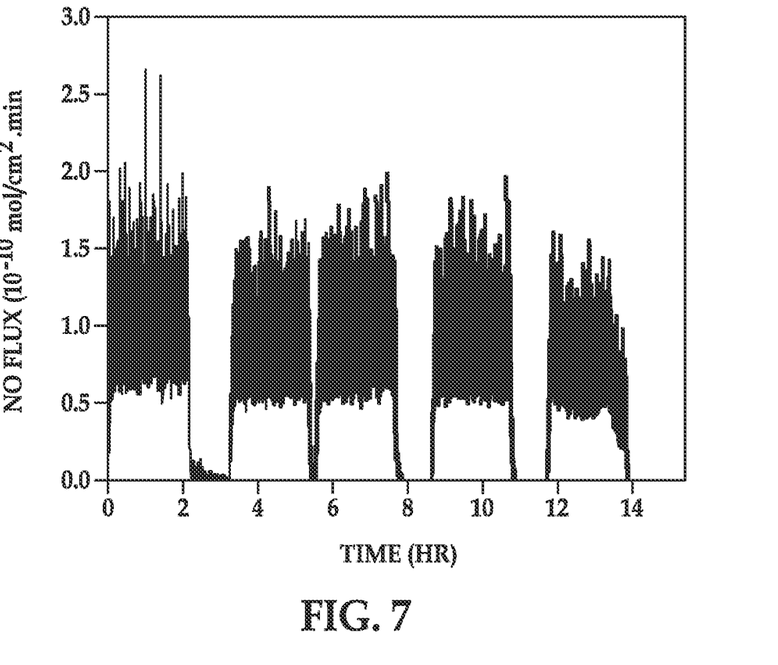
FIG. 7 is a graph illustrating the nitric oxide flux from another example of the nitric oxide delivery device over a 14 hour period.

A cathodic voltage (−1.2 V vs. NHE) was applied to the working electrode for about 30 seconds, and then an anodic voltage (+0.2 V vs. NHE) was applied to the working electrode for about 30 seconds. The pulse sequence was performed over a 14 hour period. The pulse sequence was initiated for about 2 hours at hours 0, 7 and 12, and for about 5 hours from hour 3 to hour 8. The NO flux from the surface of the silicone rubber tubing is shown in FIG. 7. The results shown in FIG. 7 illustrate that the potential applied to the copper coated electrode can be controlled to turn on or off the release of NO through the walls of the silicone rubber tubing. The silicone rubber tubing provided a barrier against the leaching of nitrite from the catheter, but also allowed for the electrochemically generated NO gas to readily diffuse out of the catheter.

Example 5

A bacterial biofilm dispersal study was performed using four NO generating catheters and one strain of bacteria, namely *E. coli*.

For each catheter, a silicone rubber tubing (2 cm length, 0.51 mm inner diameter, and 0.94 mm outer diameter) was sealed at one end with silicone rubber sealant. A 2 cm long polytetrafluoroethylene (PTFE)-coated silver/silver chloride wire was used as the reference electrode, and a 2 cm long PTFE-coated copper wire was used as the working electrode. The bare silver/silver chloride wire had an outer diameter of 0.125 mm, and the coated silver/silver chloride wire had an outer diameter of 0.176 mm. The bare copper wire had an outer diameter of 0.127 mm, and the coated copper wire had an outer diameter of 0.152 mm. The PTFE was removed from the ends of the silver/silver chloride wire and the copper wire in 20 mm lengths to expose the bare electrodes. The exposed ends of the respective wires were coiled separately. The coiled ends were inserted into the silicone rubber tubing so that the silver/silver chloride wire and the copper wire were not in direct metallic connection.

A source of nitrite was loaded into the tubing. The source of nitrite included 1 M $NaNO_2$, 0.138 M NaCl, 0.02 M EDTA in 1 M phosphate buffered saline (PBS). The pH was adjusted to 6.8 with NaOH or using appropriate ratios of phosphate salts.

The silicone rubber tubing was then sealed to form the catheter. PTFE-coated silver/silver chloride wire and PTFE-coated copper wire extended out of the silicone rubber tubing as respective leads to the reference and working electrodes.

The experiment was performed over a 2 day period with continuous flow of media (80 mL/hr) using a drip-flow bioreactor. The catheters were immersed in the media containing *E. coli*. Two of the catheters were connected to a potentiostat and a pulse sequence was applied to the respective working electrodes for 3 hours after two days in the flowing media with the cells without generating NO. These catheters are referred to as the NO releasing catheters. One cycle of the pulse sequence included 30 seconds at −1.2 V vs. Ag/AgCl wire, and 30 seconds at +0.2 V vs. Ag/AgCl wire. These NO releasing catheters were able to generate an average NO flux of $1.2*10^{-10}$ $mol/cm^2*min$ when this pulse sequence was applied. The other two catheters were used as controls. These control catheters contained the same nitrite salt solution and wires, but were not connected to potentiostats.

At the end of the 2 day period, one NO generating catheter and one control catheter were used for detection of viable bacteria on the catheter surfaces by a plate counting method. The other NO generating and control catheters were used for imaging. In particular, these two catheters were stained with fluorescent dyes (SYTO-9 and propidium iodide) for 20 minutes in the dark. The catheters were put on a glass slide before being observed with a fluorescence microscope equipped with Fluorescent Illumination System (X-cite 120, EXFO) and appropriate filter sets.

Figure 8A:
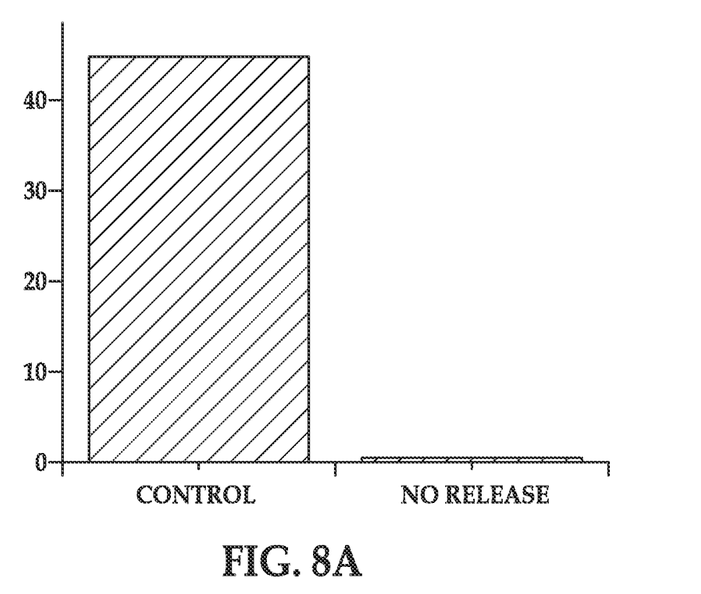
FIGS. 8A and 8B are graphs illustrating the effect of nitric oxide mediated *E. Coli* biofilm dispersal.

FIG. 8A illustrates the results observed for the one control catheter and the one NO releasing catheter obtained by the fluorescence imaging of total bacteria on the respective surfaces. As shown in FIG. 8A, the fluorescent imaging experiments indicate a dramatic reduction in number of cells left on the surface for the NO releasing catheter.

Figure 8B:
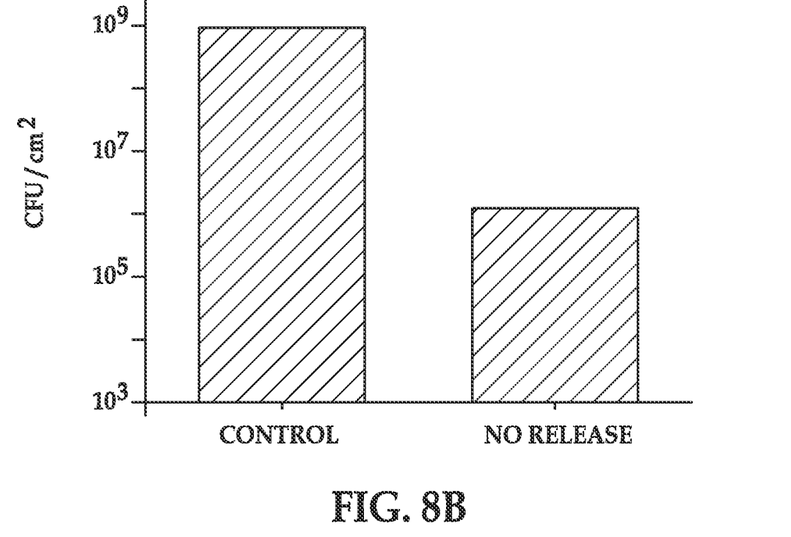

FIG. 8B illustrates the bacterium counting results (Colony Forming Units, CFU) after 2 days for the other control catheter and the other NO releasing catheter. The bacterium counting results (FIG. 8B) illustrate that NO generating catheters that were turned on for only 3 hours of NO release had nearly a 3 log unit reduction in the number of living *E. coli* cells on their surface compared to the control.

Both the fluorescence imaging and the bacterium counting results demonstrate the effectiveness of using the electrochemically modulated NO release catheter to disperse bacteria biofilm after they have formed on the surface. In particular, the results indicate the effectiveness using a one-time application of the NO release cycle for a relatively short period of time.

Example 6

A surface of a silicone rubber tubing (0.541 μm inner diameter, and 940 μm outer diameter) was modified by impregnating the tubing with tetradodecylammonium tetrakis (4-chlorophenyl) borate (ETH 500) and dioctyl sebacate (DOS) in an m-xylene solution. Impregnation was allowed to take place for 24 hours, and then the tubing was air-dried overnight inside of a fume-hood. The dried tubing was then put in an oven of 120° C. for about 1 hour.

A source of nitrite was loaded into the tubing. The source of nitrite included 1 M $NaNO_2$, 0.138 M NaCl, 20 mM EDTA in 1 M phosphate buffered saline (PBS).

Two cm long of 127 μm PTFE-coated copper and PTFE-coated Ag/AgCl wires were then inserted inside the tube containing the source of nitrite. The tube was sealed at the open end with a silicone sealant and was cured overnight at room temperature. A portion of each of the wires extended out of the silicone rubber tubing as respective leads to the reference and working electrodes.

The control catheter was the same type of surface modified catheter with the same source of nitrite and the same electrodes inserted inside the tubing, but the NO release was never electrochemically initiated.

The catheter and control catheter put inside respective drift flow bioreactors to grow biofilm on the respective surfaces. A standard or double junction commercial Ag/AgCl reference electrode was also placed inside the same channel with the catheter, and with the control catheter. 10% live bacteria was then passed through the respective channels. The background open circuit potential (BOCP) was measured for 30 minutes vs. the respective external Ag/AgCl reference electrode. The chambers were then inoculated with *E. Coli* bacteria for one hour and then the media was flowed through continuously again. The open circuit potential (OCP) measurement against the external Ag/AgCl reference electrode was recorded every hour.

Figure 9:
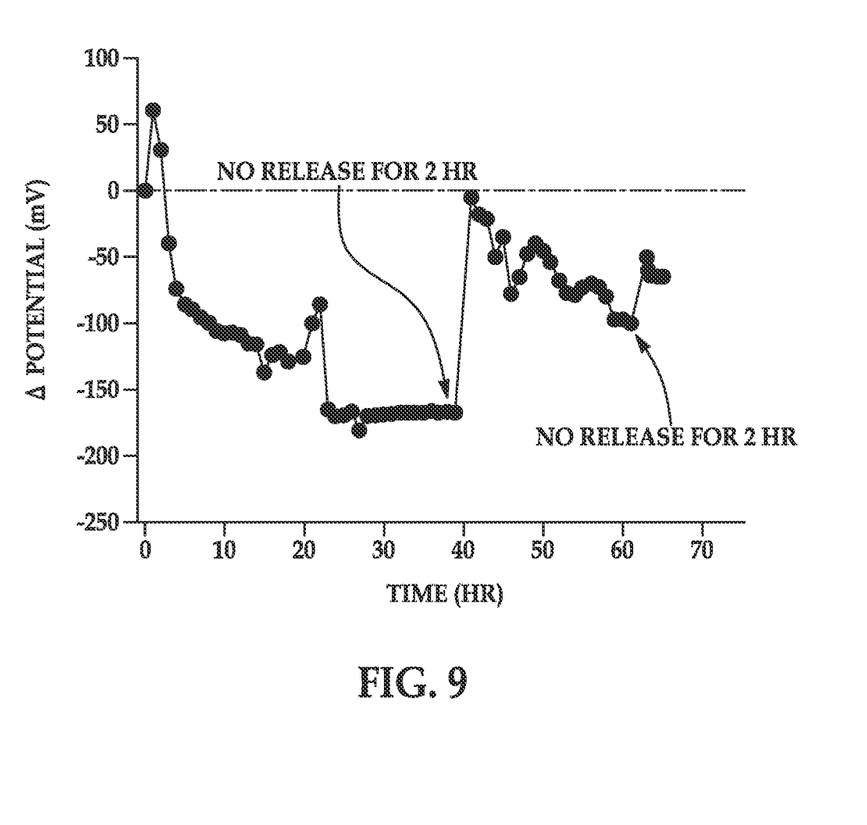
FIG. 9 is a graph illustrating the change in potential detected from an example of the catheter disclosed herein, including the potential change after two 2-hour intervals when the catheter generated nitric oxide gas.

For the sample including the catheter, when the change of 170 mV in OCP was observed from baseline (see FIG. 9), an electrochemical pulse was turned on to release NO for 2 hours. The electrochemical pulse used was −1.2 V for 30 seconds and +0.2 V for 30 seconds. The NO flux used for the first NO release was $1 \times 10^{-10}$ $moles/cm^2 \cdot min$. The OCP was measured again after stopping the electrochemical pulse.

The OCP was again measured every hour until the next event (i.e., a change in OCP) was observed. This indicated that bacteria were again starting to stick on the catheter surface. The electrochemical pulse was again turned on to release NO for 2 hours. The NO flux used for the second NO release was $0.5 \times 10^{-10}$ moles/cm$^2$·min. The electrochemical pulse used was −1.2V for 30 seconds and +0.1 for 30 seconds.

After the experiment, the catheter and the control catheter were taken out of the respective chambers and the surface bacteria were dispersed into respective solutions via a homogenizer. The solutions were plate counted to determine the number of live bacteria left on the catheter surface and the control catheter surface. The number of bacteria after the experiment with the catheter was found to be 36% less than the control.

Example 7

Five example catheters (S1-S5) and four control catheters (C1-C4) were prepared to assess the in vivo effects of electrochemical release of NO on thrombus formation. All of the example catheters and the control catheters were prepared as previously described in Example 4, except an additional length (about 3 inches) of inert tubing was attached to the top end to enable insertion of the distal tips into rabbit veins.

White rabbits (2.5-3.5 kg, Myrtle's Rabbitry, Thompson's Station, Tenn.) were used for the thrombus experiment. Intramuscular injections of 5 mg/kg xylazine injectable (AnaSed Lloyd Laboratories Shenandoah, Iowa) and 30 mg/kg ketamine hydrochloride (Hospira, Inc. Lake Forest, Ill.) were used to induce anesthesia before each rabbit experiment. Maintenance anesthesia was administered via a diluted intravenous (IV) infusion of ketamine (2 mg/ml) at a rate of 1.53 mg/kg/h. IV fluids of Lactated Ringer's were given at a rate of 33 ml/kg/h to maintain blood pressure stability.

Example catheters S1, S3, S4 and S5 and control catheters C1-C4 were implanted in rabbit jugular veins and allowed to remain in the veins for 6 hours. Example catheter S2 was implanted into a rabbit leg vein and was allowed to remain for 6 hours. For each of the Example catheters, an electrochemical pulse sequence was turned on, with the NO flux ranging from $0.8 \times 10^{-10}$ moles/cm$^2$·min to $1.1 \times 10^{-10}$ moles/cm$^2$·min to release NO. The particular NO flux at 37° C. for the respective Example catheters is shown in Table 1. For the control catheters, the electrochemical pulse sequence was turned off, with the NO flux $\ll 0.3 \times 10^{-10}$ moles/cm$^2$·min.

After the 6 hours, the example and control catheters were explanted and thrombus on each example and control catheter was recorded via digital photography. Red pixels were counted from the photo using Image J software. The surface coverage was calculated using the red pixel data, and these results are shown in Table 1.

TABLE 1

| Sample or Control | NO flux @ 37° C. | Thrombus Area/cm$^2$ | Total Area/cm$^2$ | Surface Coverage |
|---|---|---|---|---|
| S1 | ~1.1 * 10$^{-10}$ moles/cm$^2$·min | 0.021 | 0.315 | 6.7% |
| S2 | ~1.0 * 10$^{-10}$ moles/cm$^2$·min | 0.010 | 0.202 | 5.0% |
| S3 | ~1.1 * 10$^{-10}$ moles/cm$^2$·min | 0.039 | 0.202 | 19.3% |
| S4 | ~0.8 * 10$^{-10}$ moles/cm$^2$·min | 0.078 | 0.167 | 46.7% |
| S5 | ~0.9 * 10$^{-10}$ moles/cm$^2$·min | 0.083 | 0.252 | 46.7% |
| AVG. | | | | 22.12% |
| C1 | N/A | 0.214 | 0.380 | 56.3% |
| C2 | N/A | 0.263 | 0.360 | 73.1% |
| C3 | N/A | 0.690 | 1.107 | 62.4% |
| C4 | N/A | 0.165 | 0.273 | 60.2% |
| AVG. | | | | 63.0% |

As illustrated, each of the example catheters had less thrombus formation than each of the control catheters. For those example catheters when the NO flux was lower, there was a bit more thrombus formation. Overall, these results illustrate that in vivo electrochemical generation of NO reduces thrombus formation.

Figure 10A:
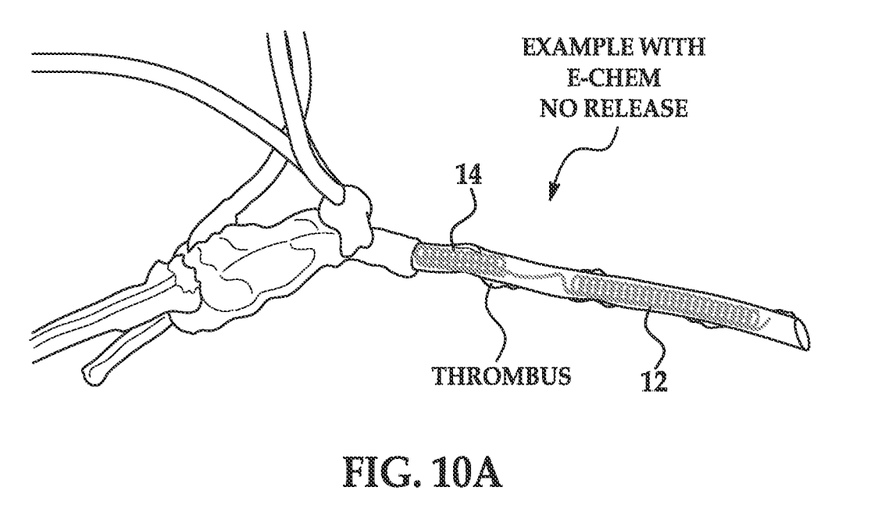
FIGS. 10A and 10B are respective representations of a photograph of an example catheter that electrochemically generated nitric oxide in vivo and of a control catheter that did not electrochemically generate nitric oxide in vivo.
Figure 10B:
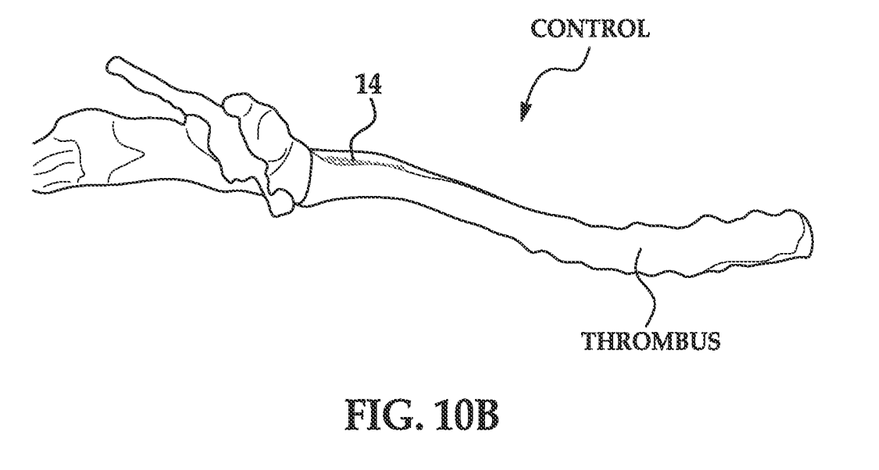

A similar experiment was performed using an example catheter and a control catheter (as previously described), except that both of the catheters were allowed to remain in the jugular veins for 8 hours. An electrochemical pulse sequence was turned on using the example catheter, but was not turned on for the control catheter. Upon extraction of the example catheter and the control catheter from the rabbit veins, digital photographs were taken. These photographs are schematically represented in FIGS. 10A and 10B. As depicted, the example catheter used to electrochemically generate NO in vivo had very little thrombus formation, as opposed to the control catheter, which was almost completely covered with thrombus.

As illustrated in these examples, nitric oxide gas can be efficiently generated from nitrite using electrodes and the two-step voltage cycle disclosed herein. The reductive cleaning of the electrode prepares the electrode for anodic liberation of Cu(I) ions, which react with nitrite to generate NO. It is believed that this process can be employed to modulate the release of NO from polymer surfaces used to prepare, for example, in-dwelling catheters. Since continuous fluxes of NO to kill or disperse biofilm forming on microbes or to prevent platelet induced clotting may not be necessary, it is believed that catheters and other medical devices disclosed herein may be utilized effectively for longer periods of time with a given supply of nitrite. This is due, at least in part, to the ability to turn the NO release on and off. It is further believed that when NO is produced at high enough levels in pulses at a defined frequency, the total moles of NO required for delivery over a given time period will be much less than the total moles of NO required with continuous release NO donor chemistry.

It is to be understood that the ranges provided herein include the stated range and any value or sub-range within the stated range. For example, a range from about 1 cm to about 2 cm should be interpreted to include not only the explicitly recited limits of about 1 cm to about 2 cm, but also to include individual values, such as 1.5 cm, 1.75 cm, etc., and sub-ranges, such as from about 1.25 cm to about 1.75 cm, etc. Furthermore, when "about" is utilized to describe a value, this is meant to encompass minor variations (up to +/−5%) from the stated value. When applied potential values are discussed, it is to be understood that wider ranges may be suitable. Increasing the magnitude of the anodic potential pulse increases the amount of Cu(I), and thus also increases the amount of NO generated. As such, it is believed that a broad range is applicable for the applied potential values, the limits of which may depend on the desired amount of Cu(I) and NO to be generated, or on the time required to clean the working electrode.

Furthermore, reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

While several examples have been described in detail, it will be apparent to those skilled in the art that the disclosed examples may be modified. Therefore, the foregoing description is to be considered non-limiting.

What is claimed is:

1. A nitric oxide delivery device, comprising:
    a housing that is permeable to nitric oxide, the housing having a surface that is modified to detect surface charge or pH, the housing defining an interior space;
    a working electrode inside of the housing interior space, the working electrode being a copper-containing conductive material or a base material coated with a copper-containing conductive material;
    a reference/counter electrode inside of the housing interior space and electrically isolated from the working electrode; and
    a source of nitrite ions contained within the housing interior space and in contact with the working electrode;
    wherein the housing surrounds the working electrode, the reference/counter electrode, and the source of nitrite ions, and separates the source of nitrite ions from an external environment.

2. The nitric oxide delivery device as defined in claim 1 wherein the delivery device is a single lumen catheter or a multi-lumen catheter.

3. The nitric oxide delivery device as defined in claim 1 wherein the housing is silicone rubber, and wherein a wall of the housing is modified with a lipophilic cation/anionic salt and a plasticizer.

4. The nitric oxide delivery device as defined in claim 3 wherein the lipophilic cation/anionic salt is tetradodecylammonium tetrakis (4-chlorophenyl) borate or tridodecylmethylammonium tetrakis (bis-trifluormethylphenyl borate), and wherein the plasticizer is dibutyl sebacate, dioctyl sebacate, or nitrophenyloctyl ether.

5. The nitric oxide delivery device as defined in claim 1, further comprising circuitry electrically connected to the working electrode and the reference/counter electrode to detect a shift in potential that exceeds a threshold value, and in response to the detection, selectively apply a voltage to the working electrode versus the reference/counter electrode.

6. The nitric oxide delivery device as defined in claim 1, further comprising:
    an external reference electrode operatively positioned outside of the housing; and
    a high impedance voltmeter operatively connected to the reference/counter electrode and the external reference electrode to detect a surface charge change or a pH change occurring at the surface that is modified to detect surface charge or pH.

7. The nitric oxide delivery device as defined in claim 1, further comprising:
    a conductive lead electrically connected to the working electrode and extending outside of the housing; and
    a second conductive lead electrically connected to the reference/counter electrode and extending outside of the housing.

8. The nitric oxide delivery device as defined in claim 7 wherein:
    the conductive lead has a polymer coating thereon;
    another polymer coating is established on both i) the second conductive lead such that an end of the second conductive lead remains exposed, and ii) an area of the reference/counter electrode that is adjacent to the working electrode; and
    another area of the reference/counter electrode remains exposed, wherein the another area of the reference/counter electrode is separate from the area of the reference/counter electrode that is adjacent to the working electrode.

9. The nitric oxide delivery device as defined in claim 1, further comprising a seal operatively attached to the housing.

10. The nitric oxide delivery device as defined in claim 1 wherein the source of nitrite ions is any water soluble, inorganic nitrite salt in an aqueous solution or a hydrogel.

11. The nitric oxide delivery device as defined in claim 1 wherein a wall of the housing is doped with a proton ionophore and from about 10 mol % to about 50 mol %, relative to the ionophore, of any tetraphenylborate species.

12. The nitric oxide delivery device as defined in claim 11 wherein the proton ionophore is tridodecylamine (TDDA).

13. The nitric oxide deliver device as defined in claim 1 wherein the working electrode is a printed ink of the copper-containing conductive material.

* * * * *